(12) United States Patent
Lee et al.

(10) Patent No.: US 11,451,075 B2
(45) Date of Patent: Sep. 20, 2022

(54) CHARGING APPARATUS WITH PHYSIOLOGICAL SIGNAL MEASURING FUNCTION

(71) Applicant: Singular Wings Medical Co., Ltd., Hsinchu County (TW)

(72) Inventors: Chen-Hao Lee, Hsinchu County (TW); Yung-Jing Hsiao, Hsinchu County (TW)

(73) Assignee: Singular Wings Medical Co., Ltd., Hsinchu County (TW)

( * ) Notice: Subject to any disclaimer, the term of this patent is extended or adjusted under 35 U.S.C. 154(b) by 786 days.

(21) Appl. No.: 15/838,373

(22) Filed: Dec. 12, 2017

(65) Prior Publication Data

US 2019/0115776 A1 Apr. 18, 2019

(30) Foreign Application Priority Data

Oct. 13, 2017 (TW) .................................. 106135217

(51) Int. Cl.
*H02J 7/00* (2006.01)
*A61B 5/00* (2006.01)
(Continued)

(52) U.S. Cl.
CPC ............ *H02J 7/0044* (2013.01); *A61B 5/282* (2021.01); *A61B 5/332* (2021.01); *A61B 5/6843* (2013.01);
(Continued)

(58) Field of Classification Search
CPC ....... H02J 7/0044; H02J 7/0042; A61B 5/282; A61B 5/332; A61B 5/6843; A61B 5/6898;
(Continued)

(56) References Cited

U.S. PATENT DOCUMENTS

| 5,505,202 A | * | 4/1996 | Mogi | A61B 5/282 |
| | | | | 600/390 |
| 2005/0209523 A1 | * | 9/2005 | Umeda | A61B 5/332 |
| | | | | 600/509 |

(Continued)

FOREIGN PATENT DOCUMENTS

| CN | 101931246 | * 12/2010 |
| CN | 105310683 | 2/2016 |

(Continued)

OTHER PUBLICATIONS

"Office Action of Taiwan Counterpart Application," dated Aug. 7, 2018, p. 1-p. 4.

(Continued)

*Primary Examiner* — Richard Isla
*Assistant Examiner* — Manuel Hernandez
(74) *Attorney, Agent, or Firm* — JCIPRNET (57) ABSTRACT

A charging apparatus is adapted to sense a physiological signal of a user. The charging apparatus includes a body, a first sensing electrode, a second sensing electrode, and a measuring device. The body has a first accommodating space and a charging port. The first sensing electrode and the second sensing electrode are disposed on the body. The measuring device is detachably disposed in the first accommodating space and is electrically connected to the first sensing electrode, the second sensing electrode, and the charging port. The first sensing electrode and the second sensing electrode are configured to transmit the physiological signal of the user to the measuring device. The charging port provides an external power to charge the measuring device.

9 Claims, 11 Drawing Sheets

(51) Int. Cl.
*A61B 5/282* (2021.01)
*A61B 5/332* (2021.01)
*A61B 5/053* (2021.01)

(52) U.S. Cl.
CPC ............ *A61B 5/6898* (2013.01); *A61B 5/742* (2013.01); *H02J 7/0042* (2013.01); *A61B 5/053* (2013.01); *A61B 2560/0214* (2013.01); *A61B 2560/0468* (2013.01); *A61B 2562/0209* (2013.01); *A61B 2562/0247* (2013.01)

(58) Field of Classification Search
CPC . A61B 5/742; A61B 5/053; A61B 2560/0214; A61B 2560/0468; A61B 2562/0209; A61B 2562/0247
USPC .......................................... 320/107, 114, 115
See application file for complete search history.

(56) References Cited

U.S. PATENT DOCUMENTS

| | | | | |
|---|---|---|---|---|
| 2011/0009729 | A1* | 1/2011 | Shin | A61B 5/6833 600/391 |
| 2011/0243187 | A1* | 10/2011 | Lu | G01K 1/18 374/164 |
| 2015/0073285 | A1 | 3/2015 | Albert et al. | |
| 2015/0366506 | A1* | 12/2015 | Chien | A61B 5/6833 600/392 |
| 2016/0095527 | A1* | 4/2016 | Thng | A61B 5/339 600/301 |
| 2016/0228064 | A1* | 8/2016 | Jung | A61B 5/4872 |
| 2017/0188864 | A1* | 7/2017 | Drury | A61B 5/02427 |
| 2017/0296088 | A1* | 10/2017 | Choi | A61B 5/7271 |
| 2019/0090770 | A1* | 3/2019 | Matsumura | A61B 5/282 |
| 2020/0077917 | A1* | 3/2020 | Sayani | A61B 5/335 |
| 2020/0229765 | A1* | 7/2020 | Peabody | A61B 5/6831 |
| 2020/0321793 | A1* | 10/2020 | Al-Ali | A61B 5/02233 |

FOREIGN PATENT DOCUMENTS

| | | | |
|---|---|---|---|
| CN | 205197985 | | 5/2016 |
| CN | 205197985 U | * | 5/2016 |
| TW | M528154 | | 9/2016 |
| TW | 201729753 | | 9/2017 |
| TW | 201729754 | | 9/2017 |

OTHER PUBLICATIONS

"Office Action of Taiwan Counterpart Application," dated Jul. 17, 2019, p. 1-p. 8.

* cited by examiner

CHARGING APPARATUS WITH PHYSIOLOGICAL SIGNAL MEASURING FUNCTION

CROSS REFERENCE TO RELATED APPLICATION

This application claims the priority benefit of Taiwan application serial no. 106135217, filed on Oct. 13, 2017. The entirety of the above-mentioned patent application is hereby incorporated by reference herein and made a part of specification.

BACKGROUND OF THE INVENTION

1. Field of the Invention

The invention relates to a charging apparatus. More particularly, the invention relates to a charging apparatus having a function of measuring a physiological signal.

2. Description of Related Art

Generally, a physiological signal sensing apparatus worn on a user's body usually has a matched carrier (e.g., a watch strap, a smart fabric, or a patch). When power of the physiological signal sensing apparatus is completely exhausted, the sensing apparatus has to be detached from the carrier to replace internal batteries. But if the user has to use the physiological signal sensing apparatus to measure the physiological signal at this time, and there is no power supply assembly providing power to the sensing apparatus, the measuring and monitoring time may as a result be missed. Besides, the batteries of the physiological signal apparatus are replaced frequently may cause inconvenience for the user.

SUMMARY OF THE INVENTION

The invention provides a charging apparatus which is able to simultaneously measure a physiological signal while charging.

In an embodiment of the invention, a charging apparatus is adapted to sense a physiological signal of a user and includes a body, a first sensing electrode, a second sensing electrode, and a measuring device. The body has a first accommodating space and has a charging port. The first sensing electrode is disposed on the body. The second sensing electrode is disposed on the body. The measuring device is detachably disposed in a first accommodating space and is electrically connected to the first sensing electrode, the second sensing electrode, and the charging port. The first sensing electrode and the second sensing electrode are configured to transmit the physiological signal of the user to the measuring device. The charging port provides an external power to charge the measuring device.

In an embodiment of the invention, the body includes an opening. The first accommodating space accommodates the measuring device through the opening.

In an embodiment of the invention, the first sensing electrode and the second sensing electrode are respectively disposed at different sides of the body.

In an embodiment of the invention, the first sensing electrode and the second sensing electrode are disposed at the same side of the body.

In an embodiment of the invention, the body further includes a power storage device. The power storage device is electrically connected to the charging port and the measuring device. The power storage device further charges the measuring device after being charged through the charging port.

In an embodiment of the invention, the body further includes a first conductive structure. The first conductive structure is electrically connected to the first sensing electrode and the measuring device. The first sensing electrode transmits the physiological signal of the user to the measuring device through the first conductive structure.

In an embodiment of the invention, the measuring device further includes a first electrical contact point and a second electrical contact point. The first electrical contact point is electrically connected to the first conductive structure. The second electrical contact point is electrically connected to the second sensing electrode. The measuring device receives the physiological signal transmitted from the first conductive structure and the second sensing electrode through the first electrical contact point and the second electrical contact point.

In an embodiment of the invention, the body further includes a second conductive structure and a third conductive structure. The second conductive structure is electrically connected to the charging port and the measuring device. The third conductive structure is electrically connected to the charging port and the measuring device. The charging port charges the measuring device through the second conductive structure and the third conductive structure.

In an embodiment of the invention, the measuring device further includes a first charging contact point and a second charging contact point. The first charging contact point is electrically connected to the second conductive structure. The second charging contact point is electrically connected to the third conductive structure. The measuring device receives the external power transmitted from the second conductive structure and the third conductive structure through the first charging contact point and the second charging contact point and then is charged.

In an embodiment of the invention, the body further includes a fourth conductive structure and a fifth conductive structure. The fourth conductive structure is electrically connected to the charging port and the power storage device. The fifth conductive structure is electrically connected to the charging port and the power storage device. The charging port charges the power storage device through the fourth conductive structure and the fifth conductive structure.

In an embodiment of the invention, the measuring device further includes a first charging contact point and a second charging contact point. The first charging contact point is electrically connected to the power storage device. The second charging contact point is electrically connected to the power storage device. The measuring device receives the power from the power storage device through the first charging contact point and the second charging contact point and then is charged.

Based on the above, in the embodiments of the invention, since the first sensing electrode and the second sensing electrode are disposed, the user may touch the two sensing electrodes to measure the physiological signal. In addition, the charging port can simultaneously charge the measuring device while measuring the physiological signal. Therefore, in the charging apparatus provided by the embodiments of the invention, the requirement to detach and replace the batteries in the measuring device is considerably reduced, and moreover, the measuring device may also be prevented from being unable to monitor the physiological signal owing to insufficient power in itself To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
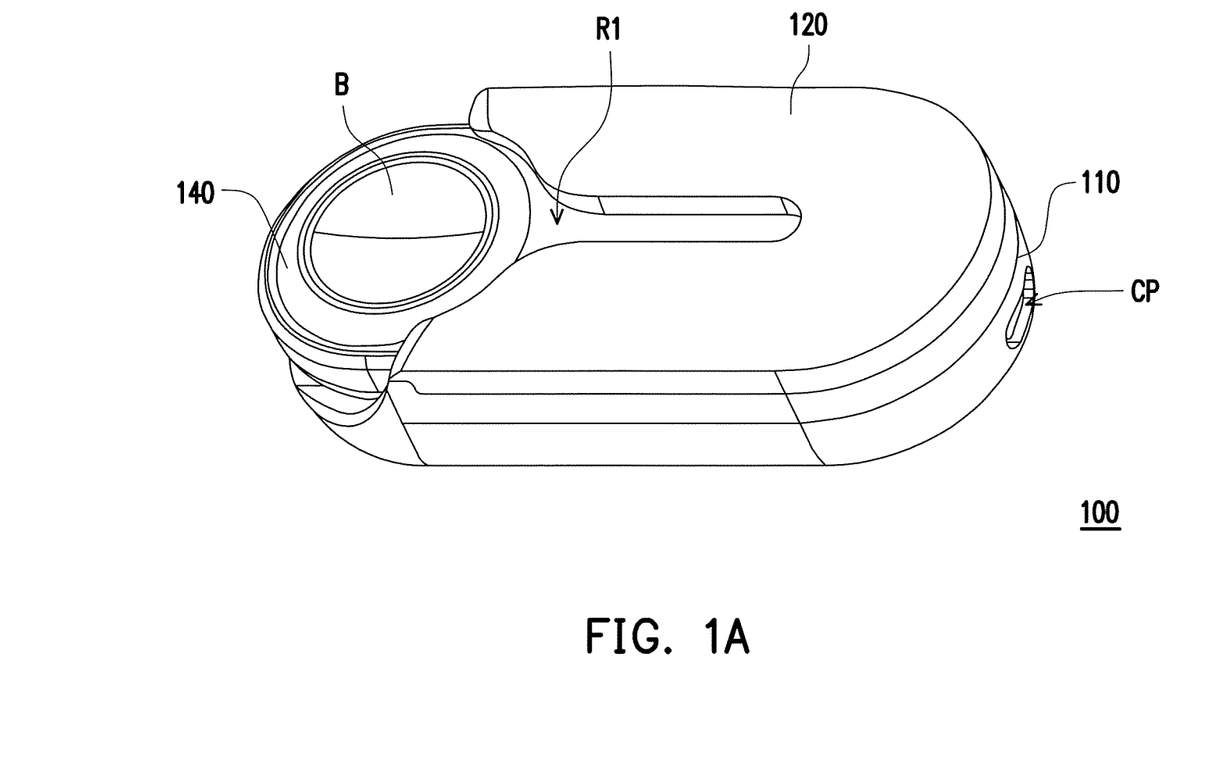
FIG. 1A is a schematic view illustrating an appearance of a charging apparatus according to an embodiment of the invention.
Figure 1B:
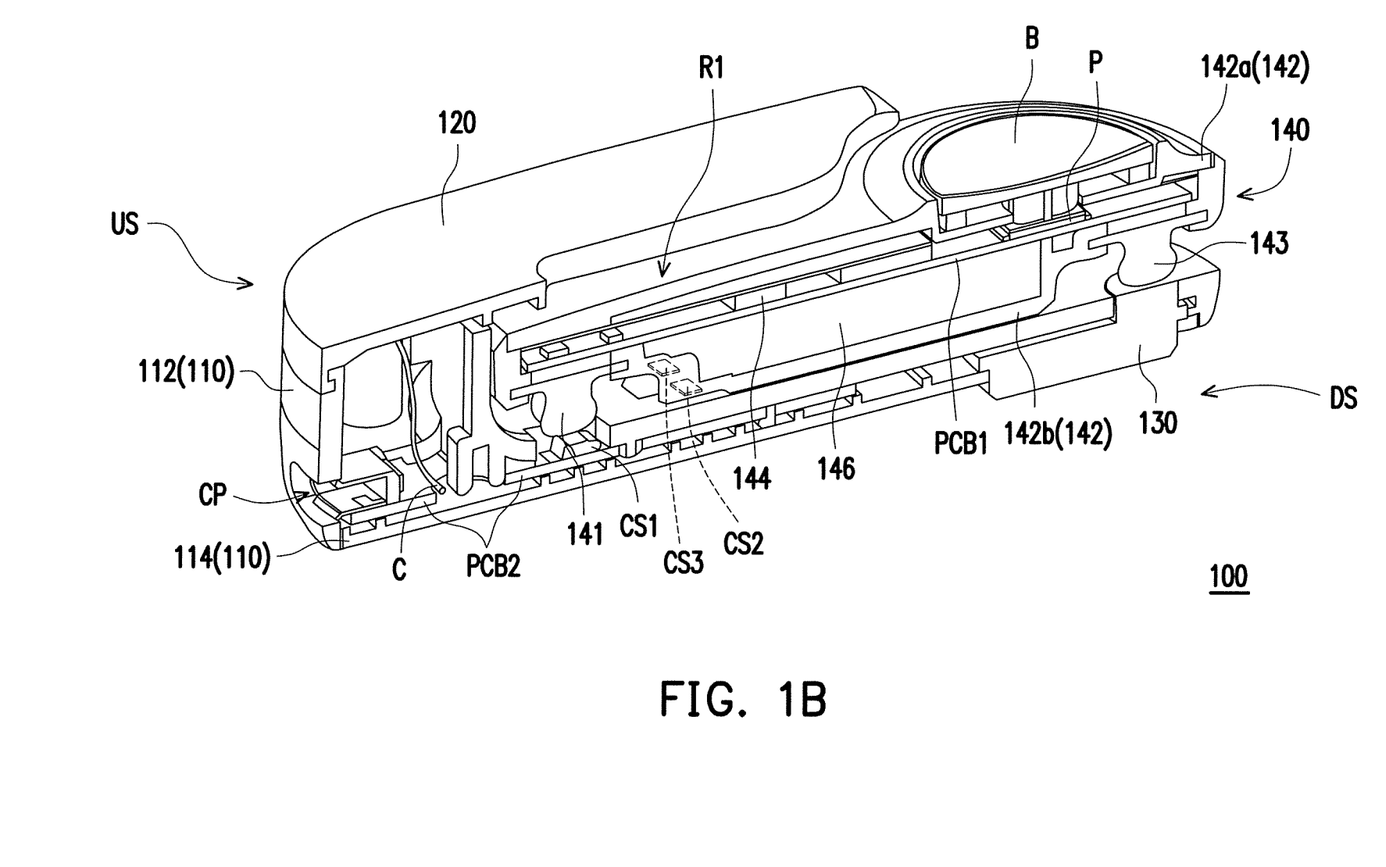
FIG. 1B is a schematic cross-sectional view illustrating the charging apparatus of FIG. 1A.
Figure 1C:
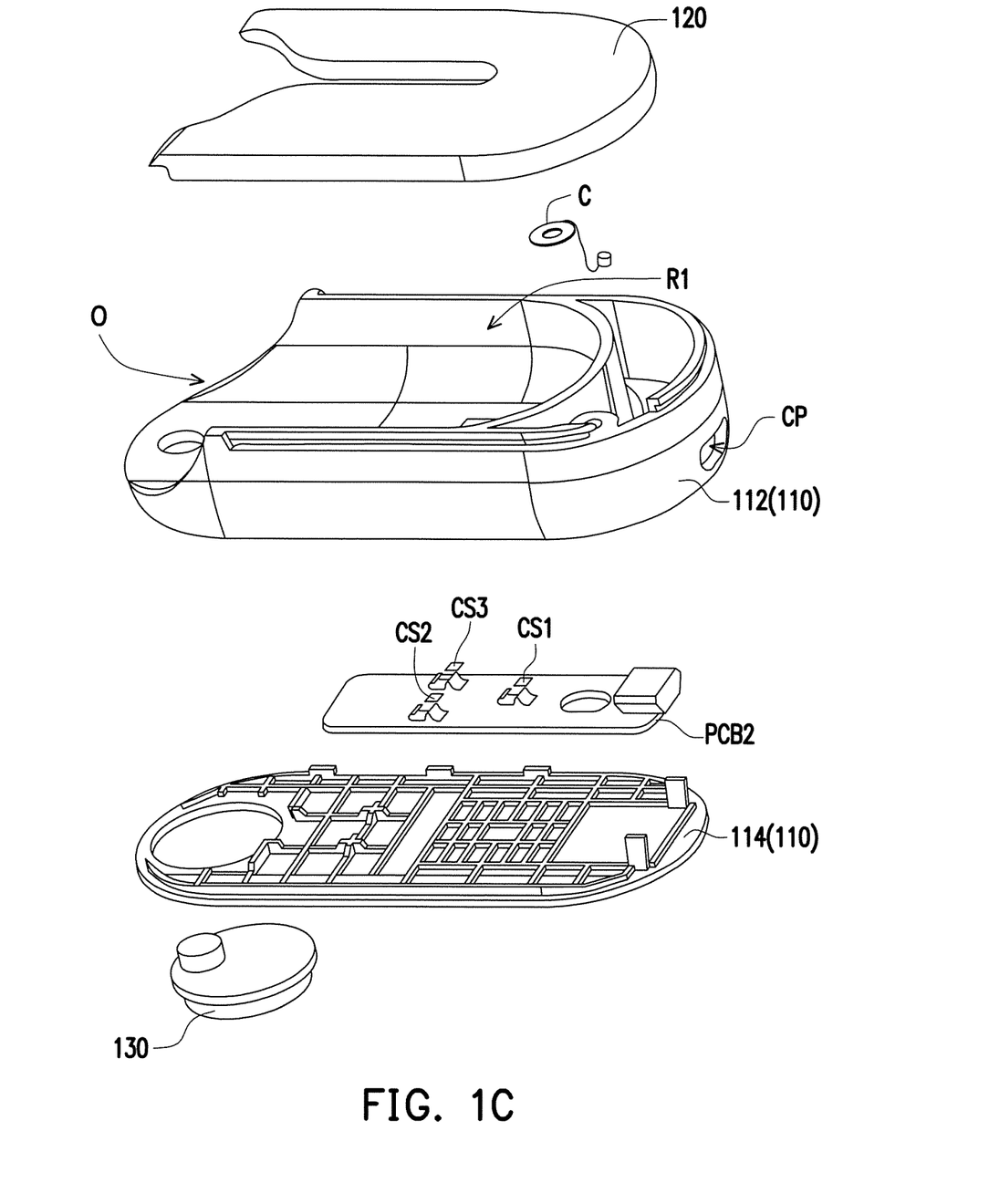
FIG. 1C is a schematic exploded view illustrating a body, a first sensing electrode, a second sensing electrode, and a first circuit board of the charging apparatus of FIG. 1A and FIG. 1B.
Figure 1D:
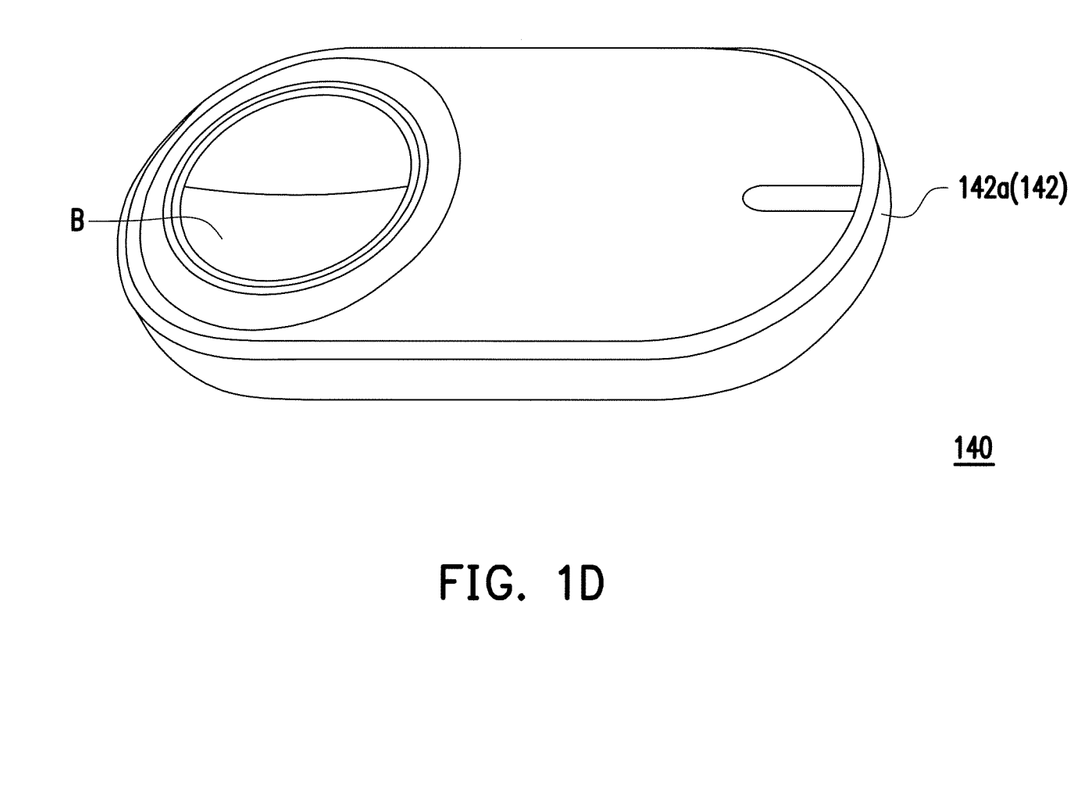
FIG. 1D is a top view illustrating a measuring device of FIG. 1A.
Figure 1E:
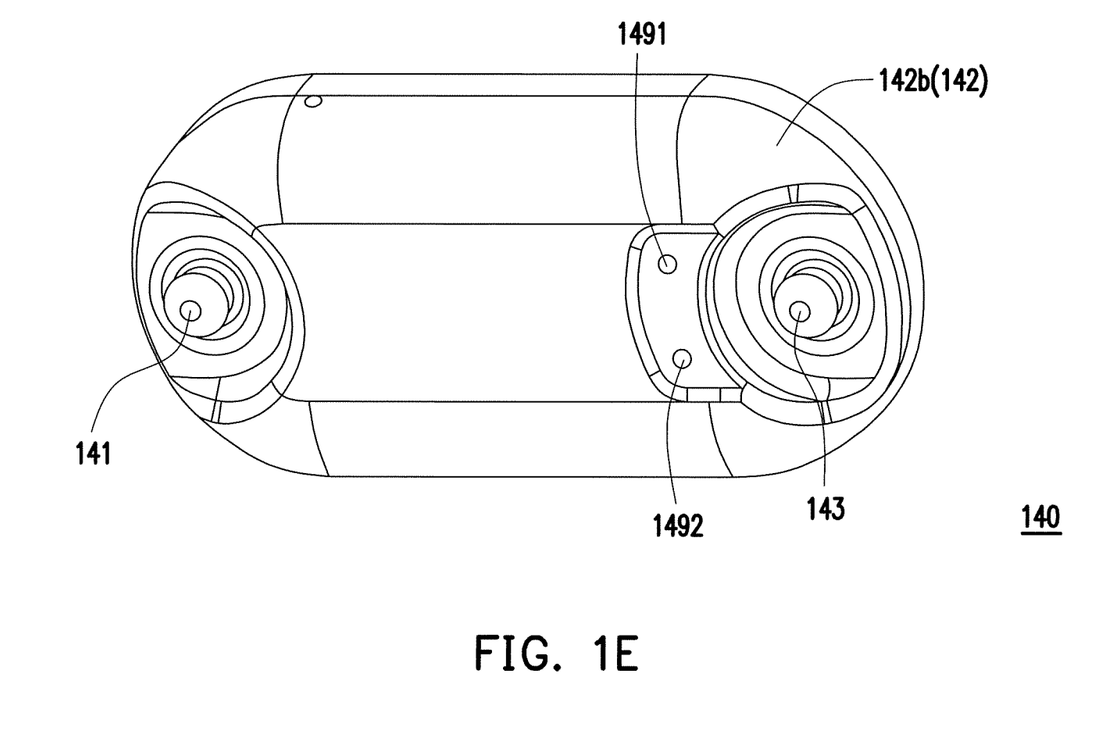
FIG. 1E is a bottom view illustrating the measuring device of FIG. 1A.
Figure 1F:
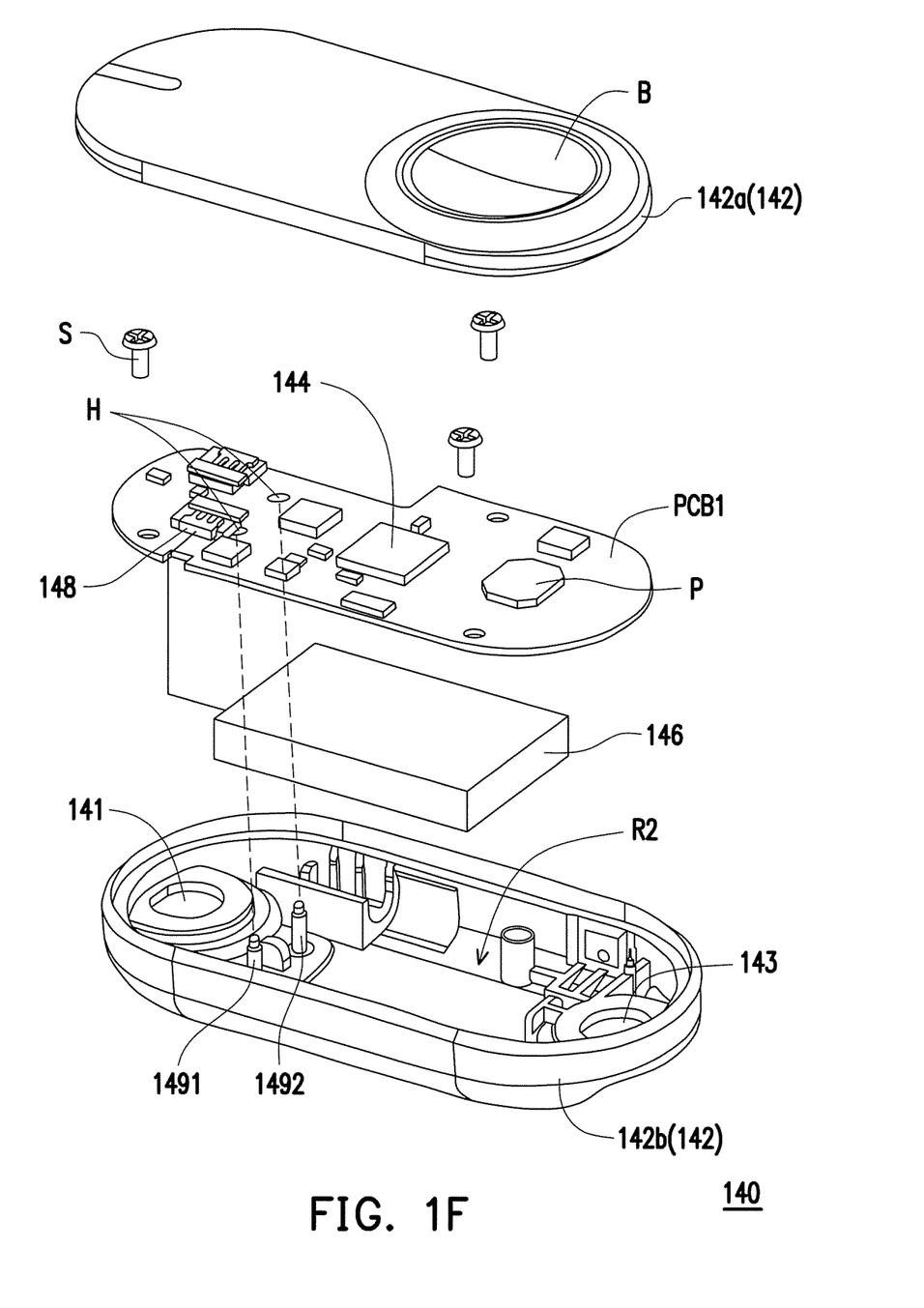
FIG. 1F is a schematic exploded view illustrating the measuring device of FIG. 1A.

FIG. 1A is a schematic view illustrating an appearance of a charging apparatus according to an embodiment of the invention. FIG. 1B is a schematic cross-sectional view illustrating the charging apparatus of FIG. 1A. FIG. 1C is a schematic exploded view illustrating a body, a first sensing electrode, a second sensing electrode, and a circuit board of the charging apparatus of FIG. 1A and FIG. 1B. FIG. 1D is a top view illustrating a measuring device of FIG. 1A. FIG. 1E is a bottom view illustrating the measuring device of FIG. 1A. FIG. 1F is a schematic exploded view illustrating the measuring device of FIG. 1A.

Referring to FIG. 1A to FIG. 1F, in the present embodiment, a charging apparatus 100 includes a body 110, a first sensing electrode 120, a second sensing electrode 130, and a measuring device 140.

The body 110 includes a main body portion 112 and a base 114, and the base 114 is located below the main body portion 112. The body 110 has a first accommodating space R1 and has an opening O. The main body portion 112 defines a portion of a border of the first accommodating space R1. The opening O is connected to an outside. That is to say, the first accommodating space R1 is an open space connected to the outside. The body 110 has a charging port CP.

The first sensing electrode 120 is disposed on the body 110 and defines another portion of the border of the first accommodating space R1. The second sensing electrode 130 is disposed on the body 110. To be specific, the first sensing electrode 120 and the second sensing electrode 130 are disposed at different sides of the body 110. The first sensing electrode 120 is disposed at an upper side US of the body 110. The second sensing electrode 130 is disposed at a lower side DS of the body 110. The main body portion 112 is located between the first sensing electrode 120 and the base 114. The base 114 is located between the second sensing electrode 130 and the main body portion 112. The first sensing electrode 120 and the second sensing electrode 130 are configured to transmit a physiological signal of a user to the measuring device 140 when being in contact with the user. The first sensing electrode 120 and the second sensing electrode 130 may be viewed as contact areas with the user.

The measuring device 140 is detachably disposed in the first accommodating space R1. The measuring device 140 includes a first electrical contact point 141, a housing 142, a second electrical contact point 143, a processor 144, a circuit board PCB1, a battery assembly 146, a connector 148, a first charging contact point 1491, a second charging contact point 1492, a button B, a pressure sensing element P, and a securing element S. The housing 142 includes an upper cover 142a and a lower cover 142b. The upper cover 142a and the lower cover 142b define a second accommodating space R2. The button B is disposed on the upper cover 142a. The first electrical contact point 141 and the second electrical contact point 143 are disposed on the lower cover 142b. The processor 144, the connector 148, and the pressure sensing element P are disposed on the circuit board PCB1. The processor 144 is connected to the battery assembly 146 through the connector 148, so as to receive the physiological signal of the user. The battery assembly 146 is located between the circuit board PCB1 and the lower cover 142b, so as to provide a power to the measuring device 140. Through holes H are provided on the circuit board PCB1. The first charging contact point 1491 and the second charging contact point 1492 are respectively aligned to the through holes H. The first charging contact point 1491 and the second charging contact point 1492 are inserted in the circuit board PCB1 through the through holes H, and are electrically connected to the circuit board PCB1. The first electrical contact point 141 and the second electrical contact point 143 protrude from the lower cover 142b. A position of the pressure sensing element P corresponds to a position located below the button B. The measuring device 140 secures the foregoing elements into the housing 142 through the securing element S.

Electrical connection relationships among the body 110, the measuring device 140, and the charging port CP of this embodiment are described in detail as follows.

The body 110 further includes a circuit board PCB2 in this embodiment. The circuit board PCB2 is located between the main body portion 112 and the base 114. The circuit board PCB2 includes a first conductive structure CS1, a second conductive structure CS2, and a third conductive structure CS3. Types of the first to the third conductive structures CS1 to CS3 are implemented as conductive elastic pieces. In other embodiments, the types may also be conductive wires, which should however not be construed as limitations to the invention. The first conductive structure CS1 electrically connected to the first sensing electrode 120 and the measuring device 140. To be more specific, the first conductive structure CS1 is electrically connected to the first sensing electrode 120 through a conductive wire C and is electrically connected to the measuring device 140 through the first electrical contact point 141. Through the second electrical contact point 143, the second sensing electrode 130 is electrically connected to the measuring device 140 through a direct contact. Next, the second conductive structure CS2 and the third conductive structure CS3 are electrically connected to the charging port CP and the measuring device. To be more specific, the first charging contact point 1491 and the second charging contact point 1492 of the measuring device 140 are respectively in contact with the second conductive structure CS2 and the third conductive structure CS3. As such, the first charging contact point 1491 and the second charging contact point 1492 are electrically connected to the second conductive structure CS2 and the third conductive structure CS3, respectively.

In this embodiment, after the user presses the button B at least longer than a predetermined period of time (e.g., 15 seconds), the pressure sensing element P senses a pressure and then triggers the measuring device 140. Then, the user may touch the first sensing electrode 120 with one part of the body (e.g., the left hand) and touch the second sensing electrode 130 with another part of the body (e.g., the right hand). As such, a complete loop is formed between the charging apparatus 100 and the user, and the processor 144 in the measuring device 140 is enabled to process and analyze the physiological signal. To be specific, the first sensing electrode 120 and the second sensing electrode 130 are configured to receive the physiological signal of the user. Next, the physiological signal of the user is transmitted to the measuring device 140 by the first sensing electrode 120 through the first conductive structure CS1 and the second sensing electrode 130 through contacting directly the second electrical contact point 143. The measuring device 140 respectively receives the physiological signal transmitted from the first conductive structure CS1 and the second sensing electrode 130 through the first electrical contact point 141 and the second electrical contact point 143. The processor 144 then processes and analyzes the physiological signal of the user received. The battery assembly 146 provides a power to the measuring device 140. The charging port CP can simultaneously charge the battery assembly 146 of the measuring device 140 through the second conductive structure CS2 and the third conductive structure CS3 while measuring. In another embodiment, when the charging apparatus 100 is not used for measuring the physiological signal, the charging port CP can still be used to charge the battery assembly 146 of the measuring device 140 through the second conductive structure CS2 and the third conductive structure CS3.

The charging apparatus 100 further includes a display interface (not shown) in this embodiment. The processor 144 is electrically connected to the display interface. The display interface can display the physiological signal of the user on the display interface, such that the user is able to monitor whether his/her physiological values are normal.

In the foregoing process, the power in the measuring device 140 (i.e., the battery assembly 146) is gradually consumed as the processor 144 continues to operate. Nevertheless, when sensing the physiological signal, the charging port CP charges the measuring device 140 simultaneously, and that the power may not be completely exhausted. Therefore, in the charging apparatus 100 of this embodiment, a requirement to detach and replace the battery assembly 146 in the measuring device 140 is considerably reduced, and moreover, the measuring device 140 may also be prevented from being unable to monitor the physiological signal owing to insufficient power in itself.

In addition, when the measuring device 140 has insufficient power but the user still has to measure the physiological signal, since the first sensing electrode 110 and the second sensing electrode 130 are disposed on the body 110, the user can install the measuring device 140 onto the charging apparatus 100 and directly touch the first sensing electrode 110 and the second sensing electrode 130 on the body 110, so as to input a signal to the measuring device 140. Besides, the charging apparatus 100 can simultaneously charge the measuring device 140. Therefore, the charging apparatus 100 of this embodiment is able to simultaneously charge the measuring device 140 while measuring the physiological signal.

It should be explained that a part of the contents in the previous embodiments are used in the following embodiments, in which repeated description of the same technical contents is omitted, and elements which are named identically may be referred the part of the contents. A detailed description will not be repeated in the following embodiments.

Figure 2A:
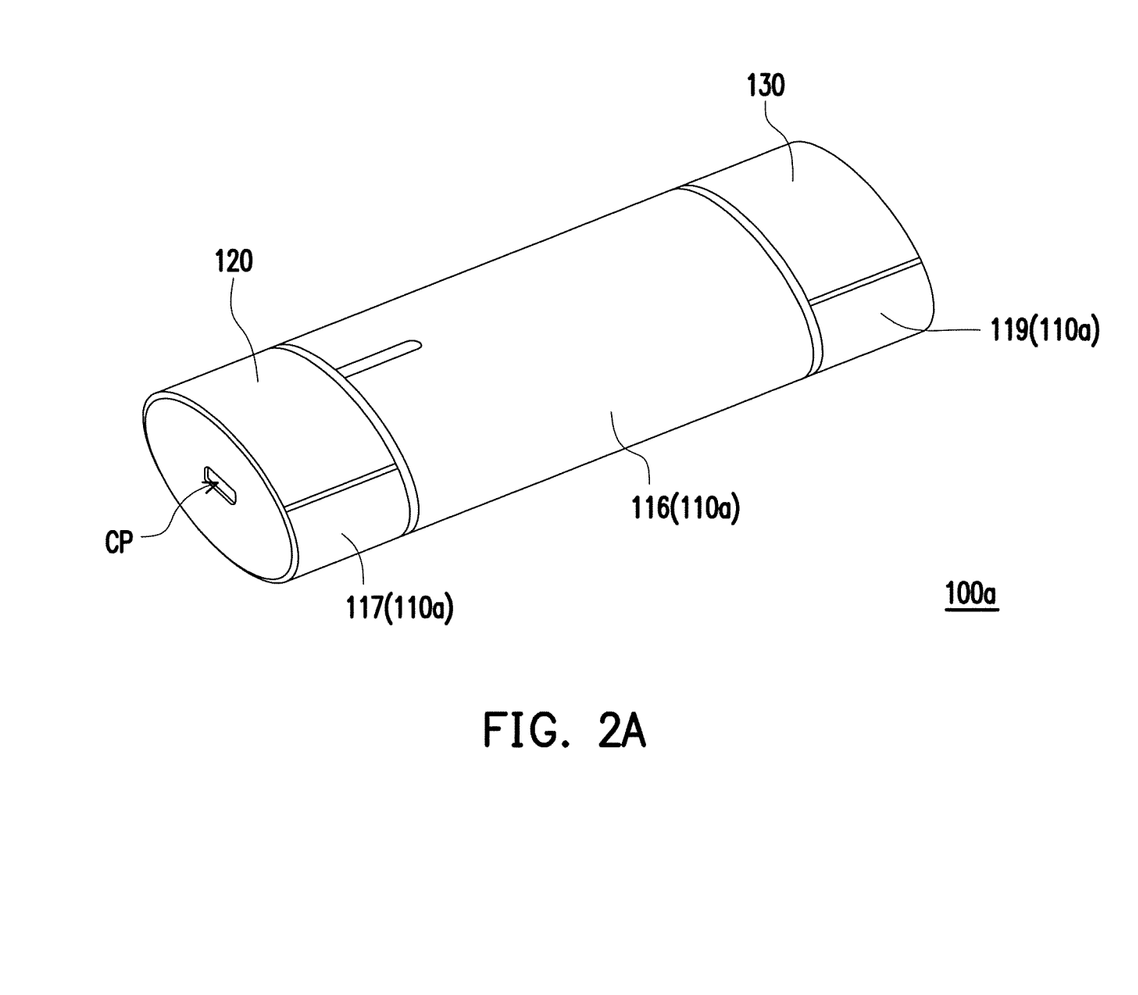
FIG. 2A is a schematic view illustrating an appearance of a charging apparatus according to another embodiment of the invention.
Figure 2B:
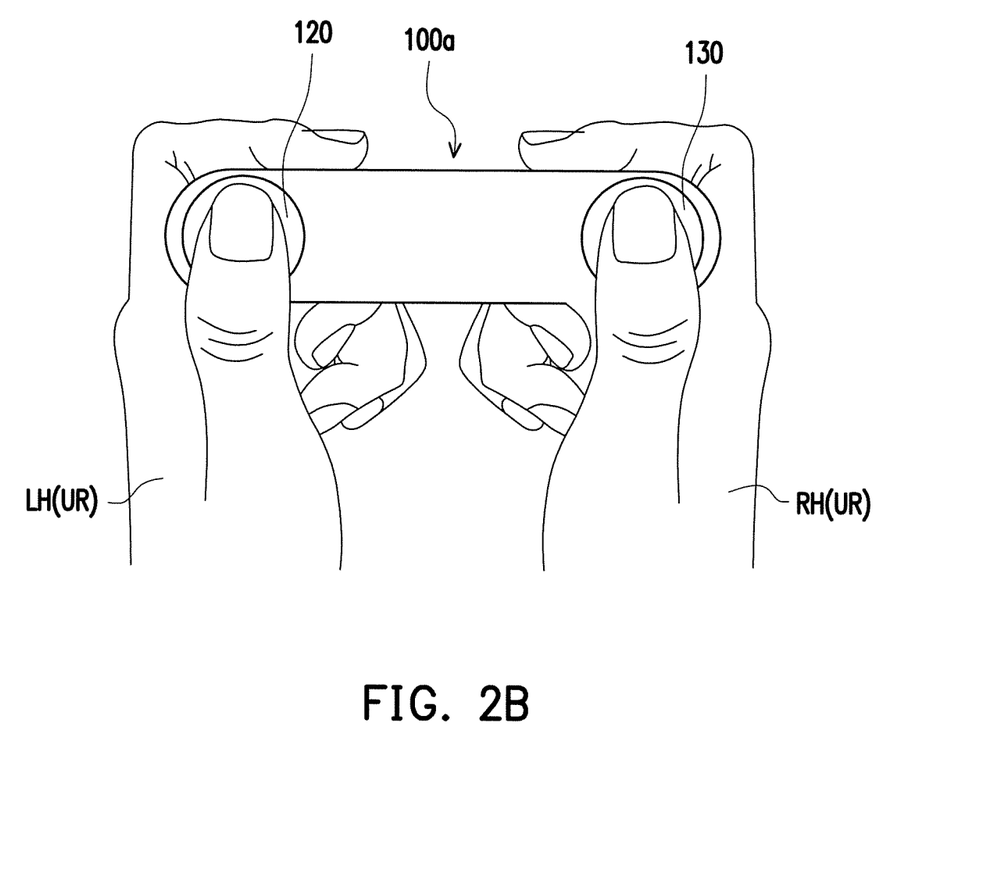
FIG. 2B is a schematic view of a user using the charging apparatus of FIG. 2A.

FIG. 2A is a schematic view illustrating an appearance of a charging apparatus according to another embodiment of the invention. FIG. 2B is a schematic view of a user using the charging apparatus of FIG. 2A.

Referring to FIG. 2A, a charging apparatus 100a illustrated in FIG. 2A is substantially similar to the charging apparatus 100 illustrated in FIG. 1A and FIG. 1B, and a difference therebetween includes that the first sensing electrode 120 and the second sensing electrode 130 are disposed at the same side of the body 110. To be specific, a body 100a includes an opening and closing portion 116 and a first end portion 117 and a second end portion 119 extending from a left side and a right side of the opening and closing portion 116. The first sensing electrode 120 is disposed on the first end portion 117. The second sensing electrode 130 is disposed on the second end portion 119. The opening and closing portion 116 has an opening and closing function. In an embodiment, the user can open the opening and closing portion 116 to place the measuring device 140 into the first accommodating space R1, and the user may close the opening and closing portion 116 to protect the measuring device 140. In another embodiment, the user may hold either the first end portion 117 or the second end portion 119 and pull it out to activate the opening and the closing portion 116 to open the first accommodating space R1. As such, the user can place the measuring device 140 into the first accommodating space R1. The invention is not intended to limit how the opening and closing portion 116 is opened or closed.

Next, referring to FIG. 2B, in this embodiment, a left hand LH of a user UR directly touches the first sensing electrode 120, and a right hand RH of the user UR directly touches the second sensing electrode 130. That is, the user UR may press the charging apparatus 100a with both hands to measure the physiological signal in this embodiment.

Figure 3A:
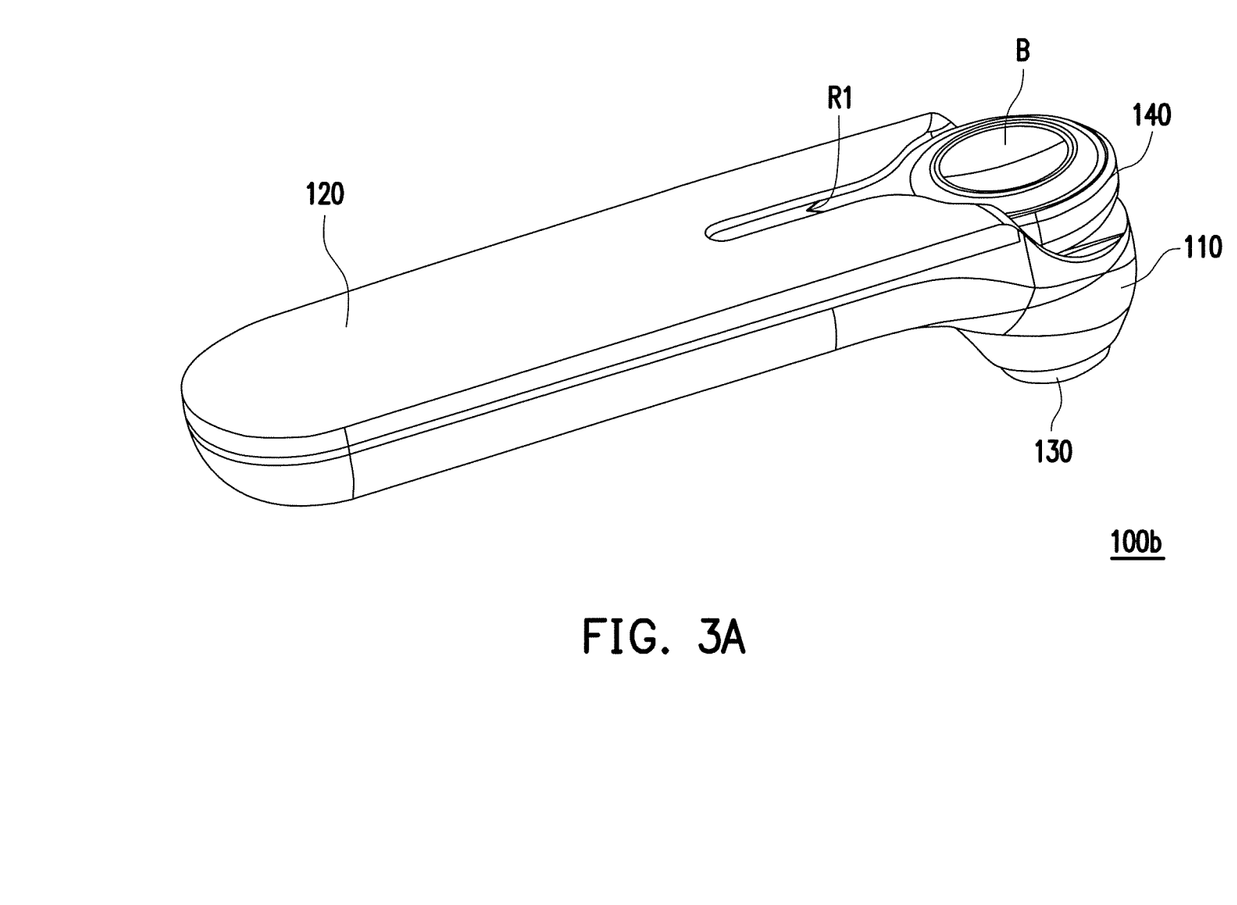
FIG. 3A is a schematic view illustrating an appearance of a charging apparatus according to yet another embodiment of the invention.
Figure 3B:
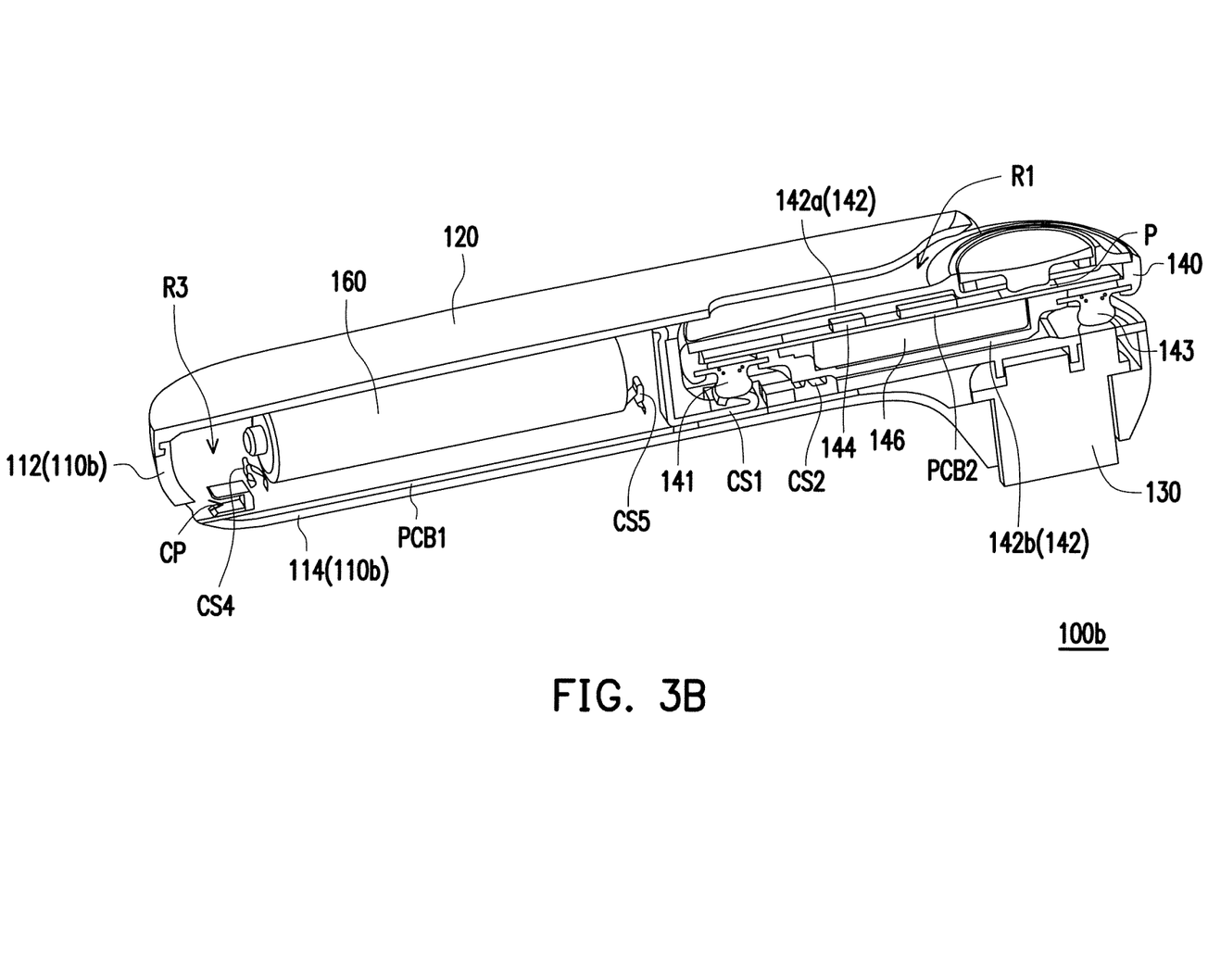
FIG. 3B is a schematic cross-sectional view illustrating the charging apparatus of FIG. 3A.
Figure 3C:
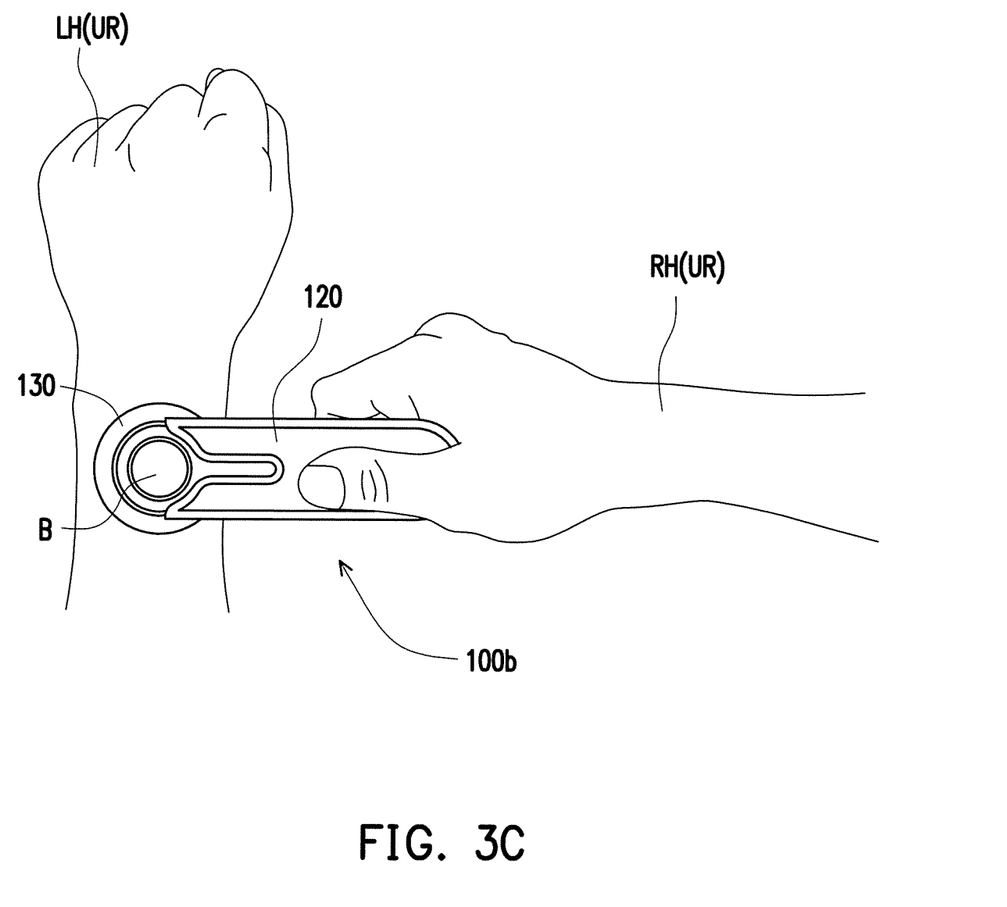
FIG. 3C is a schematic view of a user using the charging apparatus of FIG. 3A.

FIG. 3A is a schematic view illustrating an appearance of a charging apparatus according to yet another embodiment of the invention. FIG. 3B is a schematic cross-sectional view illustrating the charging apparatus of FIG. 3A. FIG. 3C is a schematic view of a user using the charging apparatus of FIG. 3A.

Referring to FIG. 3A and FIG. 3B, a charging apparatus 100b illustrated in FIG. 3A and FIG. 3B is substantially similar to the charging apparatus 100 illustrated in FIG. 1A and FIG. 1B, and a difference therebetween includes that a body 110b further includes a power storage device 160, a fourth conductive structure CS4, and a fifth conductive structure CS5. To be specific, the body 110b further includes a third accommodating space R3. The first sensing electrode 120, the main body portion 112, and the base 114 together define the third accommodating space R3. The power storage device 160 is disposed in the third accommodating space R3 and is electrically connected to the charging port CP and the measuring device 140, respectively. The fourth conductive structure CS4 and the fifth conductive structure CS5 are electrically connected to the charging port CP and the power storage device 160. The first charging contact point 1491 and the second charging contact point 1492 are further electrically connected to the power storage device 160. After the power storage device 160 is charged through the charging port CP, the power storage device 160 can further charge the battery assembly 146 in the measuring device 140. To be more specific, in this embodiment, the charging port CP charges the power storage device 160 through the fourth conductive structure CS4 and the fifth conductive structure CS5. The measuring device 140 receives the power from the power storage device 160 through the first charging contact point 1491 and the second charging contact point 1492 and then is charged. At this time, when no power supply can be provided to the user and the power in the measuring device 140 (i.e., the battery assembly 146) is gradually consumed, the power stored in the power storage device 160 may thereby be used to charge the measuring device 140.

Referring to FIG. 3C, in this embodiment, the right hand RH of the user UR may hold the base 114 and touches the first sensing electrode 120 located on the third accommodating space R3. The second sensing electrode 130 may be in direct contact with the left hand LH of the user UR. In other words, the user UR may simply hold the charging apparatus 100b with single hand to measure the physiological signal in this embodiment.

In view of the foregoing, in the charging apparatus provided by the embodiments of the invention, since the charging port is disposed on the body, the measuring device can be charged by the charging port. Therefore, in the charging apparatus provided herein, the requirement to detach and replace the batteries in the measuring device is considerably reduced, and moreover, the measuring device may also be prevented from being unable to monitor the physiological signal owing to insufficient power in itself. In addition, since the first sensing electrode and the second sensing electrode are disposed on the body of the charging apparatus, the user may directly touch the first sensing electrode and the second sensing electrode on the body, so as to input the signal to the measuring device. Moreover, the charging apparatus can simultaneously charge the measuring device while measuring.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A charging apparatus adapted to sense a physiological signal of a user, the charging apparatus comprising:
    a body, having a charging port, a main body portion, a base, and an upper side relative to the base, wherein the main body portion, the base, and the upper side form a first accommodating space and define a border of the first accommodating space, and an opening is provided on one side of the first accommodating space, so that the first accommodating space is an open space;
    a first sensing electrode, disposed on the body;
    a second sensing electrode, disposed on the body; and
    a measuring device, detachably disposed in the first accommodating space and electrically connected to the first sensing electrode, the second sensing electrode, and the charging port,
    wherein the first sensing electrode and the second sensing electrode are configured to transmit the physiological signal of the user to the measuring device, the charging port provides an external power to charge the measuring device,
    wherein the body further comprises:
    a first conductive structure, electrically connected to the first sensing electrode through a conductive wire and the measuring device,
    wherein the first sensing electrode transmits the physiological signal of the user to the measuring device through the first conductive structure, and
    wherein the measuring device further comprises:
        a first electrical contact point, electrically connected to the first conductive structure; and
        a second electrical contact point, electrically connected to the second sensing electrode through a direct contact,
        wherein the measuring device receives the physiological signal transmitted from the first conductive structure and the second sensing electrode through the first electrical contact point and the second electrical contact point.

2. The charging apparatus as claimed in claim 1, wherein the first accommodating space accommodates the measuring device through the opening.

3. The charging apparatus as claimed in claim 1, wherein the first sensing electrode and the second sensing electrode are disposed at different sides of the body.

4. The charging apparatus as claimed in claim 1, wherein the first sensing electrode and the second sensing electrode are disposed at the same side of the body.

5. The charging apparatus as claimed in claim 1, wherein the body further comprises:
    a power storage device, electrically connected to the charging port and the measuring device, wherein the power storage device further charges the measuring device after being charged through the charging port.

6. The charging apparatus as claimed in claim 5, wherein the body further comprises:
    a fourth conductive structure, electrically connected to the charging port and the power storage device; and
    a fifth conductive structure, electrically connected to the charging port and the power storage device,
    wherein the charging port charges the power storage device through the fourth conductive structure and the fifth conductive structure.

7. The charging apparatus as claimed in claim 6, wherein the measuring device further comprises:
    a first charging contact point, electrically connected to the power storage device; and
    a second charging contact point, electrically connected to the power storage device,
    wherein the measuring device receives a power from the power storage device through the first charging contact point and the second charging contact point and then is charged.

8. The charging apparatus as claimed in claim 1, wherein the body further comprises:
    a second conductive structure, electrically connected to the charging port and the measuring device; and a third conductive structure, electrically connected to the charging port and the measuring device, wherein the charging port charges the measuring device through the second conductive structure and the third conductive structure.

9. The charging apparatus as claimed in claim 8, wherein the measuring device further comprises:

a first charging contact point, electrically connected to the second conductive structure; and a second charging contact point, electrically connected to the third conductive structure, wherein the measuring device receives the external power transmitted from the second conductive structure and the third conductive structure through the first charging contact point and the second charging contact point and then is charged.

\* \* \* \* \*